United States Patent [19]
Calabrese

[11] Patent Number: 6,071,255
[45] Date of Patent: *Jun. 6, 2000

[54] FLAT CERVICAL COLLAR HAVING A UNITARY CHIN SUPPORT

[75] Inventor: Salvatore Calabrese, Philadelphia, Pa.

[73] Assignee: Philadelphia Cervical Collar Company, Westville, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/556,781

[22] Filed: Nov. 2, 1995

Related U.S. Application Data

[63] Continuation-in-part of application No. 08/255,360, Jun. 8, 1994, Pat. No. 5,622,529.

[51] Int. Cl.⁷ .................................................. A61F 13/00
[52] U.S. Cl. ................................. 602/18; 128/DIG. 23
[58] Field of Search ...................... 128/DIG. 23; 602/6, 602/17, 18

[56] References Cited

U.S. PATENT DOCUMENTS

| | | |
|---|---|---|
| Re. 32,219 | 8/1986 | Garth . |
| 3,070,090 | 12/1962 | Taylor ........................... 128/DIG. 23 |
| 3,343,532 | 9/1967 | Zumaglini .................. 128/DIG. 23 X |
| 3,504,667 | 4/1970 | McFarlane ............................... 602/18 |
| 3,622,057 | 11/1971 | Marker . |
| 3,756,226 | 9/1973 | Calabrese et al. . |
| 4,205,667 | 6/1980 | Graylord, Jr. ............................ 602/18 |
| 4,325,363 | 4/1982 | Berkeley . |
| 4,401,111 | 8/1983 | Blackstone . |
| 4,413,619 | 11/1983 | Garth . |
| 4,538,597 | 9/1985 | Lerman .................................... 602/18 |
| 4,628,913 | 12/1986 | Lerman .................................... 602/18 |
| 4,702,233 | 10/1987 | Omicioli . |
| 4,712,540 | 12/1987 | Tucker et al. . |
| 4,745,922 | 5/1988 | Taylor . |
| 4,886,052 | 12/1989 | Calabrese . |
| 4,940,043 | 7/1990 | Burns et al. . |
| 4,987,891 | 1/1991 | Gaylord, Jr. et al. . |
| 5,010,877 | 4/1991 | Druskoczi . |
| 5,038,759 | 8/1991 | Morgenstern . |
| 5,058,572 | 10/1987 | Schmid et al. . |
| 5,060,637 | 10/1991 | Schmid et al. . |
| 5,083,553 | 1/1992 | Stevenson et al. . |
| 5,180,361 | 1/1993 | Moore et al. . |
| 5,201,702 | 4/1993 | Mars ........................................ 602/18 |
| 5,215,517 | 6/1993 | Stevenson et al. ...................... 602/18 |
| 5,230,698 | 7/1993 | Garth . |
| 5,275,581 | 1/1994 | Bender .................................... 602/18 |
| 5,437,612 | 8/1995 | Moore et al. ............................ 602/18 |
| 5,520,619 | 5/1996 | Martin ................................. 602/18 X |
| 5,622,529 | 4/1997 | Calabrese ................................ 602/18 |
| 5,632,722 | 5/1997 | Tweardy et al. ........................ 602/18 |

*Primary Examiner*—Richard J. Apley
*Assistant Examiner*—Denise Pothier
*Attorney, Agent, or Firm*—Wolf, Block, Schorr and Solis-Cohen LLP; Kenneth DeRosa

[57] ABSTRACT

A cervical collar is provided having a front collar portion fabricated from a substantially incompressible plastic resin and a compressible, flexible foam strip mounted on one side of the front body section. The front collar portion includes a mandible support portion comprising a chin support portion extending transversely in an upper central portion of the front collar portion and a pair of laterally extending jaw support portions which connect at their distal ends to side portions of the front collar portion. Each jaw support portion includes at least one opening formed therein for facilitating bending of the jaw support to conform to a wearer's jaw line.

11 Claims, 12 Drawing Sheets

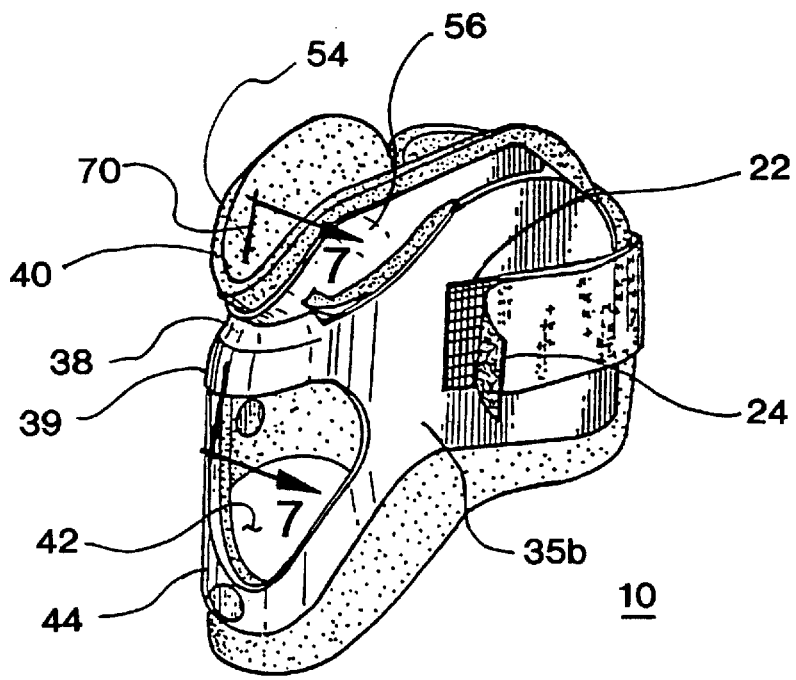
FIG. 6
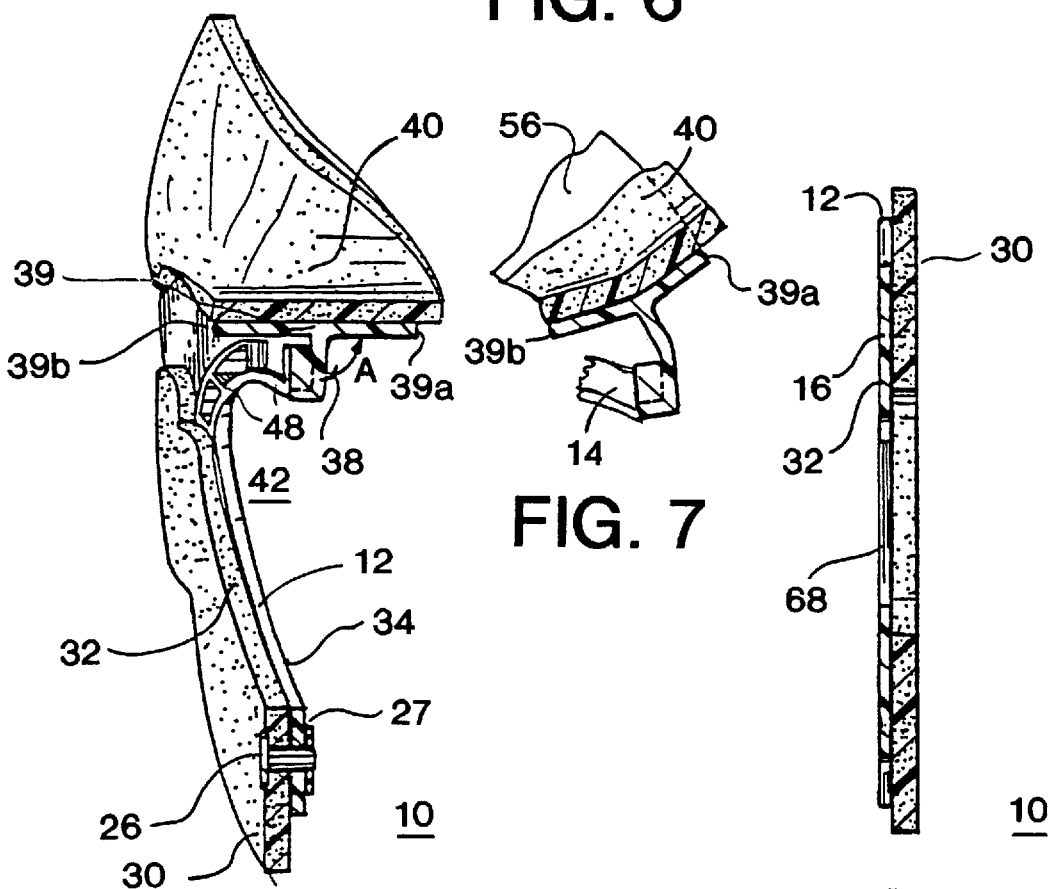
FIG. 7
FIG. 4
FIG. 5

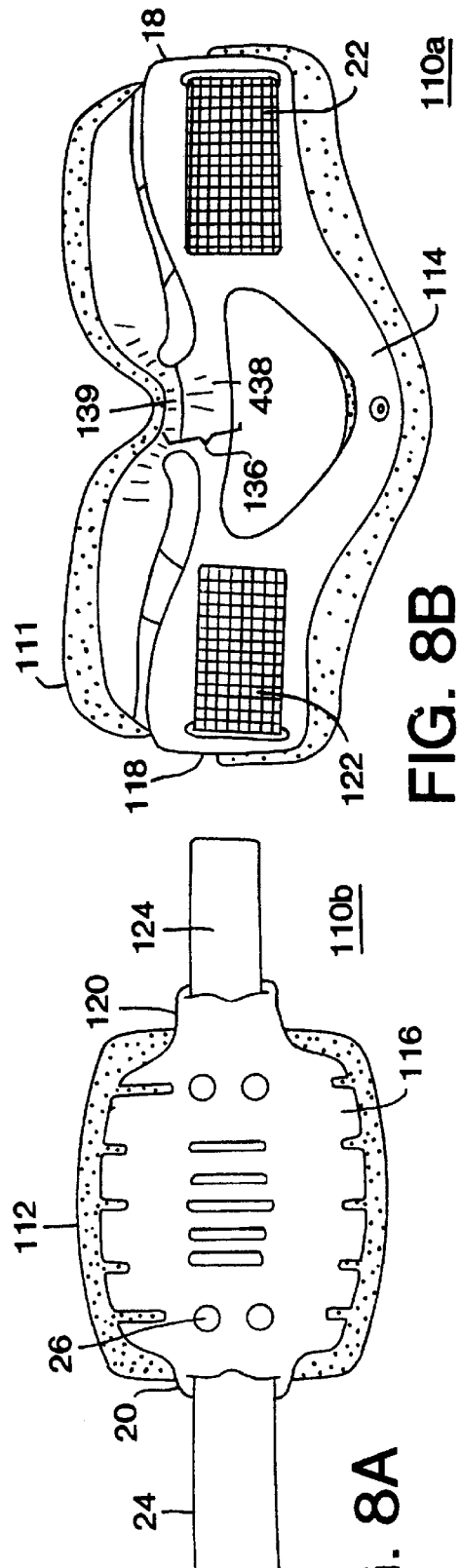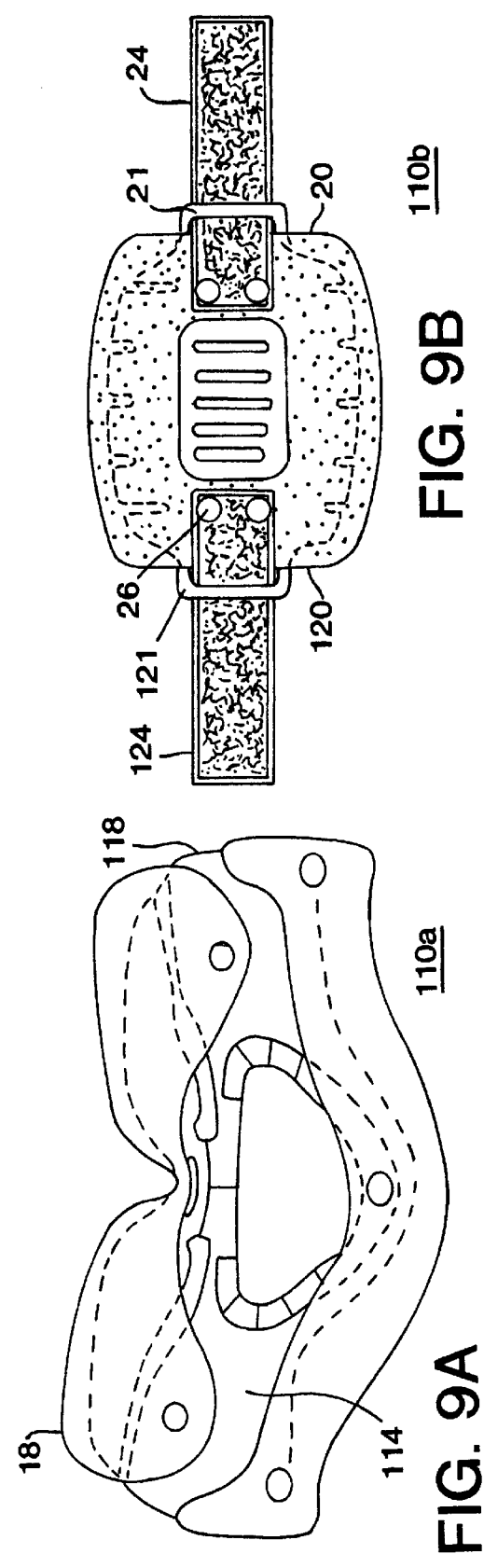

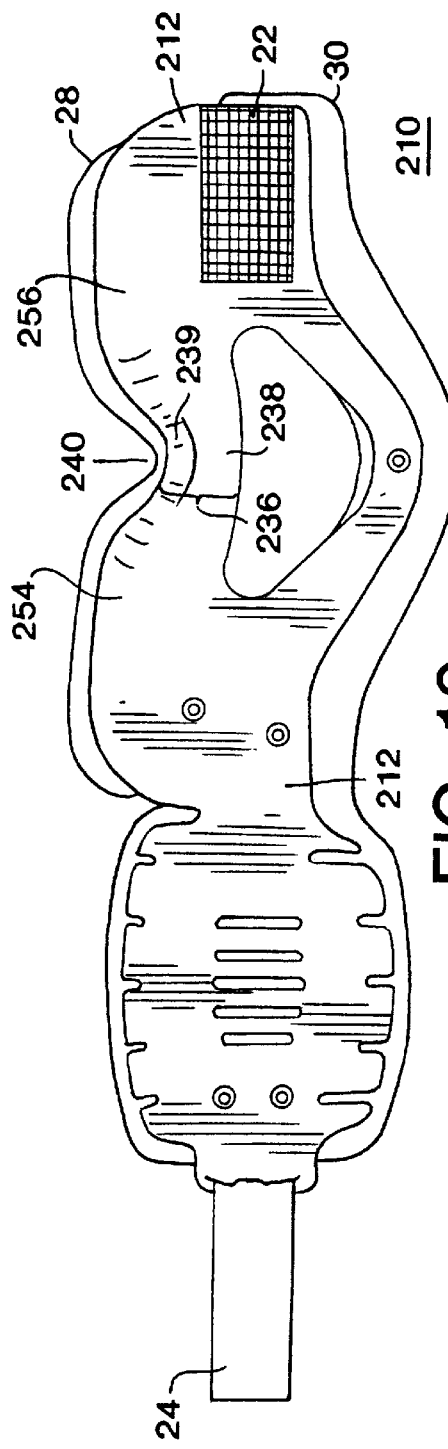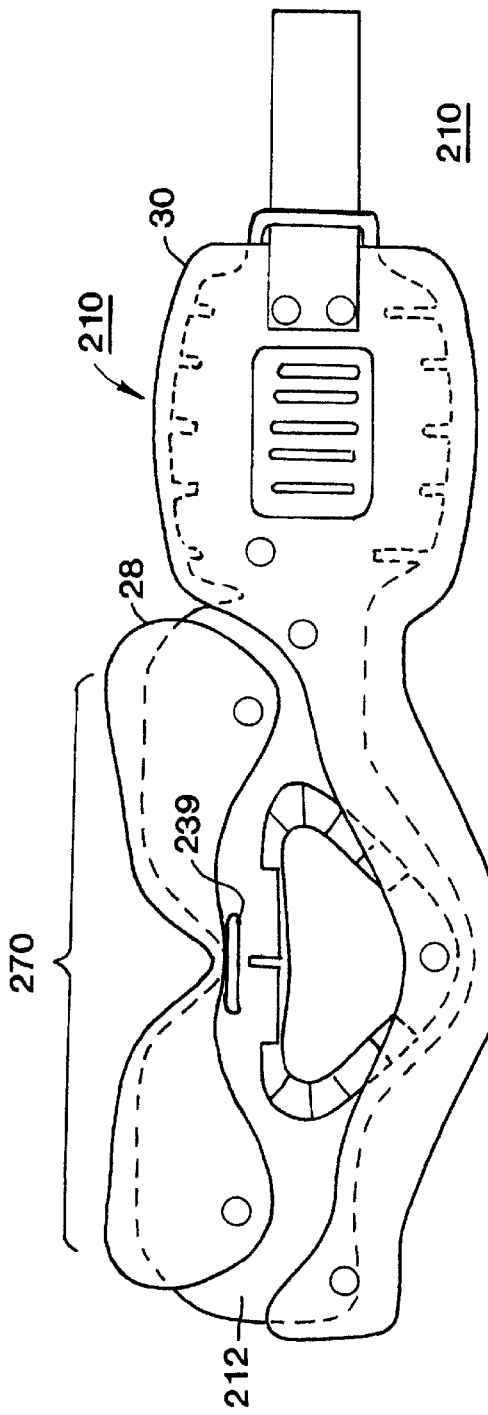

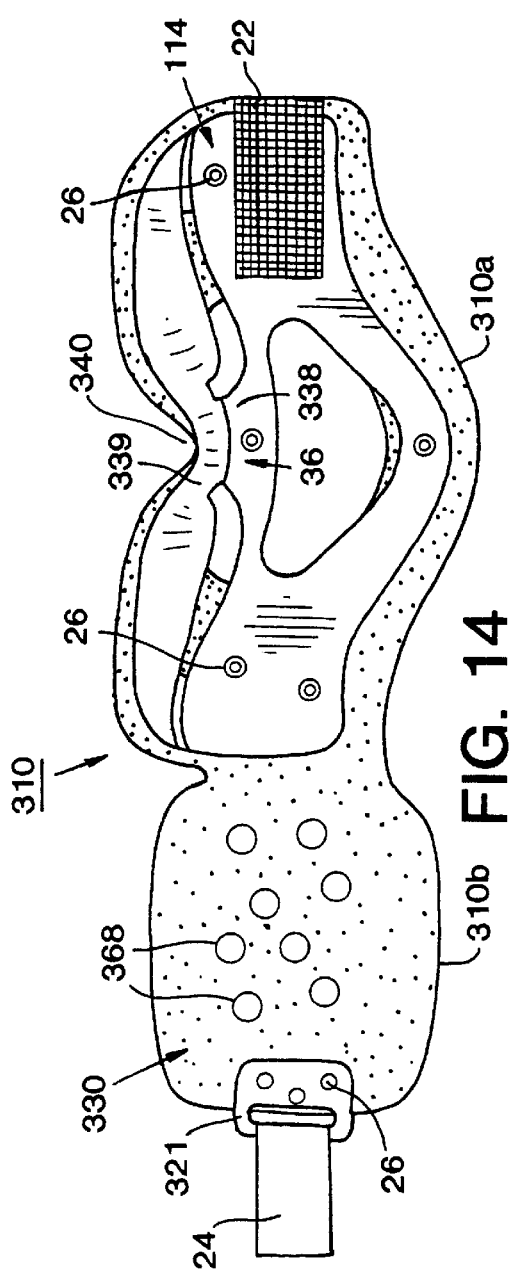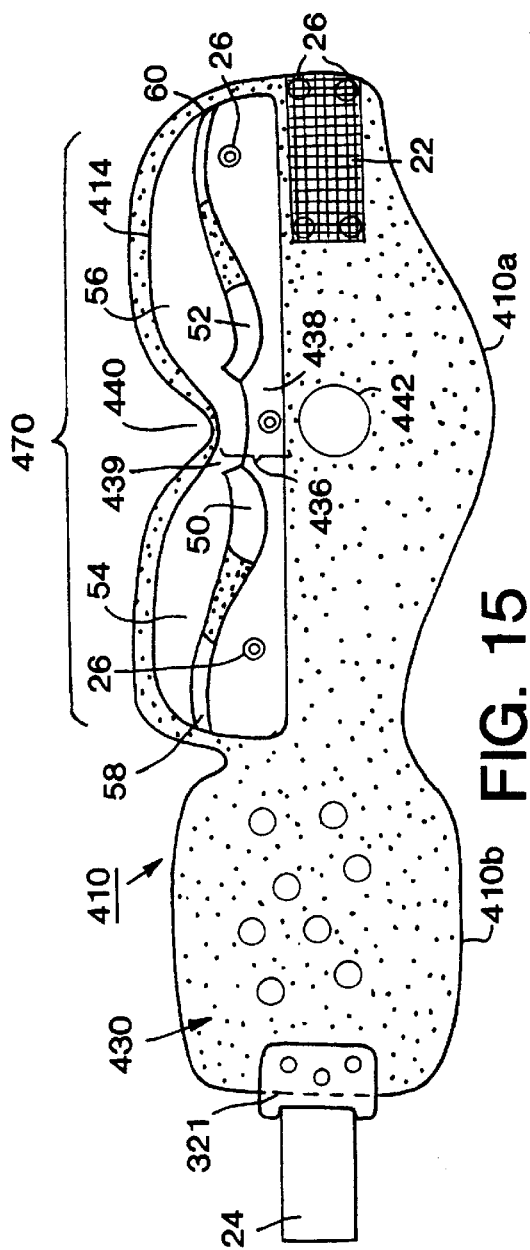

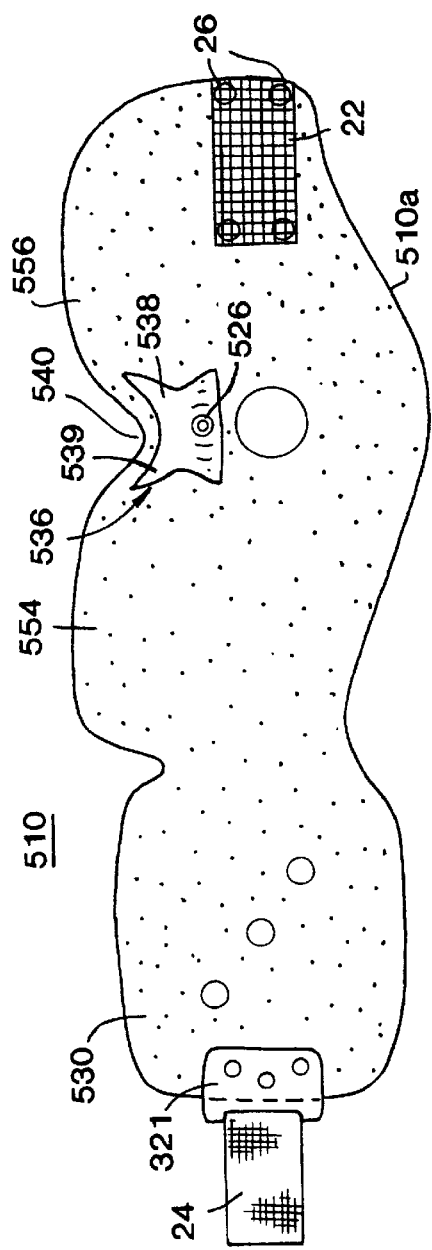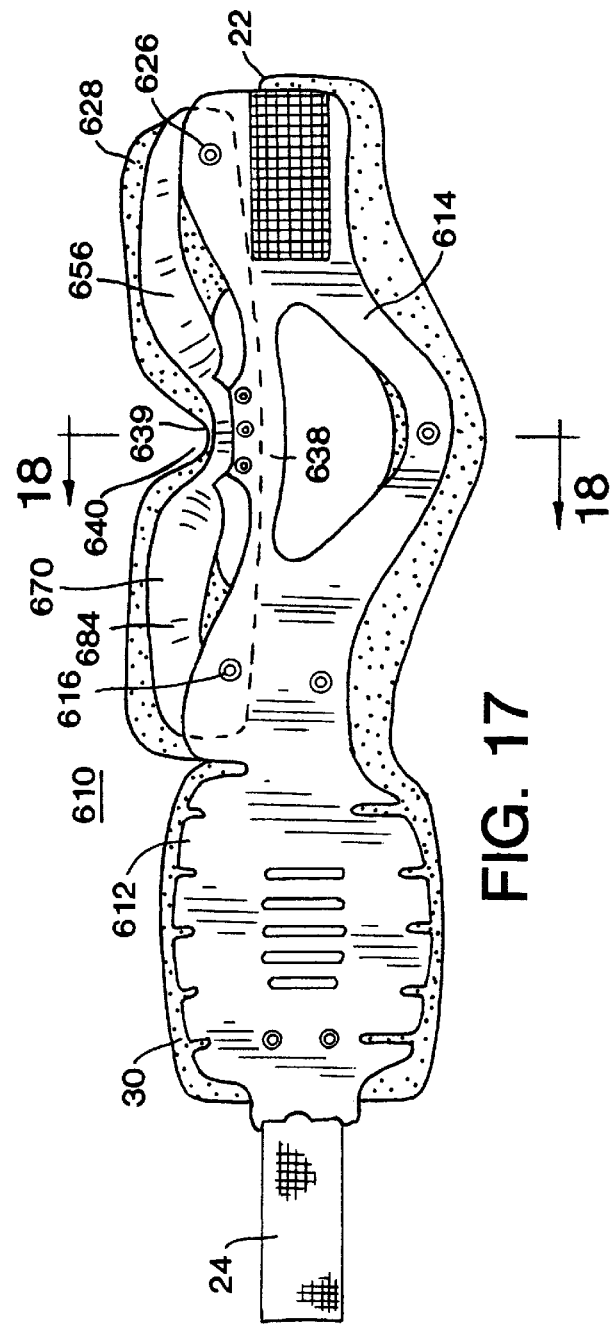

FLAT CERVICAL COLLAR HAVING A UNITARY CHIN SUPPORT

CROSS REFERENCE INFORMATION

This is a continuation-in-part of co-pending U.S. patent application Ser. No. 08/255,360, which was filed on Jun. 8, 1994, entitled "*One-Piece Cervical Collar*," now U.S. Pat. No. 5,622,529.

FIELD OF THE INVENTION

The present invention relates to orthopaedic restraints and, in particular, to cervical collars.

BACKGROUND OF THE INVENTION

Lightweight, plastic cervical collars come in a variety of designs Traditional two-piece collars of the type shown in U.S. Pat. Nos. 3,756,226 and 4,886,052 use semi-circular body halves to provide cervical support. From the method disclosed by U.S. Pat. No. 3,622,057, the body halves are fabricated by shaping pliable cross-linked foam. Despite their acknowledged successful performance, such two-piece collars are considered less desirable than other cervical collars for certain uses. In particular, such collars are considered undesirable for use in emergency vehicles where their relative bulk makes them difficult to store and because of the difficulties that arise from trying to slip a semi-circular rear collar half beneath the neck of an accident victim at the same time the emergency care providers are trying to immobilize the victim.

A number of cervical collars have been designed to respond to this problem. These include, for example, those shown in U.S. Pat. Nos. 4,413,619; 4,712,540; 4,987,891; 5,060,637; and 5,215,517. Such collars typically include unitary front and rear body sections cut from a non-foamed, relatively stiff, yet flexible, plastic sheet. A hybrid cervical collar as shown in U.S. Pat. No. 5,083,553 has also been designed to respond to this need. The two-piece collar disclosed in that patent includes separate front and rear body sections cut from stiff, flexible plastic sheets.

The above-described collars generally comprise a body section fabricated from a resiliently flexible flat plastic sheet material and an integrally attached chin support which is also typically fabricated from a flat plastic sheet material. The integrally attached chin support is either mechanically fastened to, or monolithically formed with a front portion of the body section, joining it at the distal ends of the chin support. However, since the chin supports on these collars are typically provided as a flat structure, they must be folded into a cup-shape and mechanically fastened at a central portion of the front body section.

Thus, while certain cervical collars known in the prior art are easy to store and easy to position beneath the neck of an accident victim, it is believed that such collars do not provide the comfort and support provided by traditional two-piece, semi-circular designs.

Moreover, these prior art cervical collars all suffer from a number of drawbacks, especially with respect to the chin support area. The existing collars have mechanically fastened chin supports which results in inadequate support, lack of stability, and decreased reliability. The inadequate under chin support provided by existing collars cause the head of the wearer to slip from the chin support into the interior of the collar. Further, the mechanically connected chin support of the existing collars causes increased flexing and decreased rigidity of the chin support and does not adequately stabilize the cervical-spinal region of the wearer. Thus, existing collars can potentially compound the wearer's spinal injuries.

Also, with continued use, the mechanical fastenings typically employed to attach the chin support to front body sections may fail and render the collar useless. Finally, the manufacturing costs associated with providing a mechanical fastening between the chin support and the front body section are relatively high because extensive manual labor is required to perform the fastening process.

Therefore, it is believed that there is a long-felt and as yet unsolved need for a substantially flat, one-piece and/or hybrid two-piece collar that can be stored more easily than conventional, semi-circular, two-piece collars but that provides more comfort and more support under the chin than provided by existing designs.

Accordingly, it is an object of the present invention to provide a flat cervical collar that eliminates the need for a mechanical fastening at the central portion and distal ends of the chin support. It is also an object of the present invention to provide a flat collar that includes a rear or inner chin support ledge which captures the surface area under the region extending from the chin to each ramus of the mandible, thereby limiting flexing of the chin support relative to the front body section and providing added stability to the cervical region.

It is a further object of the present invention to provide a process enabling the front body section and the chin support of a collar to be of unitary construction and a contoured three-dimensional configuration.

It is another object of the present invention to provide a collar with a unitary chin support and a front body section construction that minimizes material, manufacturing, and assembly costs.

It is a still further object of the present invention to provide a flat, one-piece or hybrid two-piece, cervical collar fabricated by a process that permits the thickness of components to be independently varied to control the degree of rigidity and flexibility provided by each component.

Yet another object of the current invention is to provide a flat, one-piece or hybrid two-piece, cervical collar that includes mandible supports that can move independently of the front body section and each other to more readily adapt to the jawline of a wearer.

A further object of the present invention is to provide a flat, one-piece or hybrid two-piece, cervical collar having a mandible support that includes a plurality of openings formed therein permitting the mandible support to conform to each wearer's unique jawline.

Each of the embodiments of the collar of the present invention described below satisfies at least some of these objects and all embodiments of the collar of the present invention collectively satisfy all of these objects.

SUMMARY OF THE INVENTION

It has now been found that the above and other objects are fulfilled by a cervical collar comprising a bendable front collar portion including a front body section fabricated from a substantially incompressible plastic resin and a compressible, a flexible foam strip mounted on one side of the front body section, where the front body section is molded to extend transversely outwardly at the center of the front collar portion from a substantially flat remainder of the front collar portion to define a chin support extending transversely in an upper central portion of the front collar portion. The collar also has a substantially flat, bendable rear collar portion, a fastener strip attached to a selected one of the front collar portion and the rear collar portion proximal a free edge of the selected one collar portion, and a second fastener strip matingly engageable with the first fastener strip that extends from a free edge of a remaining one of the front collar portion and rear collar portion sufficiently to engage the first fastener strip when the free edge of the front collar portion and the free edge of the rear collar portion are positioned adjoining one another.

The invention also provides a cervical collar comprising a generally elongated, bendable unitary body molded in one piece from a plastic resin having a front body section and a rear body section extending from the front body section. The unitary body has a length and flexibility that allows the body to be wrapped into a tubular shape around a wearer's neck with a free edge of the front body section preferably adjoining a free edge of the rear body section. The unitary body of the present invention, however, is substantially flat before being wrapped. The unitary body also has a central portion of its front body section molded to extend transversely from a substantially flat remainder of the body that defines a chin support extending transversely in the upper central portion of the front body section. A first fastener strip mounted to the unitary body adjoins one free edge of the body, a second fastener strip, matingly engageable with the first strip, extends from a remaining free edge of the unitary body sufficiently to overlap the first fastener when the unitary body is wrapped into the tubular shape with the free edges at least adjoining one another. A strip of a compressible flexible foam material mounted on one side of the unitary body cushions an inner side of the collar body when the collar body is wrapped into a tubular shape.

In another embodiment of the present invention, an improvement in cervical collars including a bendable front collar portion and a normally flat, bendable rear collar portion is provided. The front collar portion includes a front body section molded from plastic resin and at least one strip of a compressible flexible foam material mounted to one side of the front body section. The collar further includes a first fastener strip attached to one of the front collar portion and the rear collar portion, and a second fastener strip that is matingly engageable with the first strip extends from a free edge of a remaining one of the front and rear collar portions so as to engage the first fastener strip when the front collar portion and rear collar portion are bent together into a tubular shape around a wearer's neck. In this embodiment, the front body section is preferably pre-molded to project transversely outwardly from one side of the front collar portion between substantially co-planar edge portions to define a chin support.

In yet another embodiment of the present invention, a cervical collar is provided having a front body portion fabricated from a substantially incompressible plastic resin and a compressible, flexible foam strip mounted on one side of front body portion. The front body portion includes a mandible support portion comprising a chin support portion extending transversely in an upper central portion of the front collar portion and a pair of laterally extending jaw support portions which connect at their distal ends to side portions of the front collar portion. Each jaw support portion includes at least one opening formed therein for facilitating bending of the jaw support to conform to a wearer's jaw line.

BRIEF DESCRIPTION OF THE DRAWINGS

FIG. 4 is a cross-sectional view taken along lines 4—4 of FIG. 1;

FIG. 5 is a cross-sectional view taken along lines 5—5 of FIG. 1;

FIG. 6 is a perspective view of the collar of FIGS. 1–5 wrapped into a tubular shape as it would be when worn;

FIG. 7 is a broken away, partial cross-sectional view of the collar of FIGS. 1–6, taken along the lines 7—7 in FIG. 6;

FIG. 8A is a top plan view of the rear section of a two piece embodiment of the cervical collar of the present invention;

FIG. 8B is a top plan view of a front section of a two piece embodiment of the cervical collar of the present invention;

FIG. 9A is a bottom plan view of a front section of the two piece collar of FIG. 8B;

FIG. 9B is a bottom plan view of a rear section of the two piece collar of FIG. 8A;

FIG. 12 is a top plan view of second embodiment of a cervical collar of the present invention without mandible support openings;

FIG. 13 is a bottom plan view of the collar of FIG. 12;

FIG. 14 is a top plan view of a third embodiment of a cervical collar of the present invention;

FIG. 15 is a top plan view of a fourth embodiment of a cervical collar of the present invention;

FIG. 16 is a top plan view of a fifth embodiment of a cervical collar of the present invention;

FIG. 17 is a top plan view of a sixth another embodiment of a cervical collar of the present invention;

DETAILED DESCRIPTION OF THE PREFERRED EMBODIMENTS

Figures 1, 2:
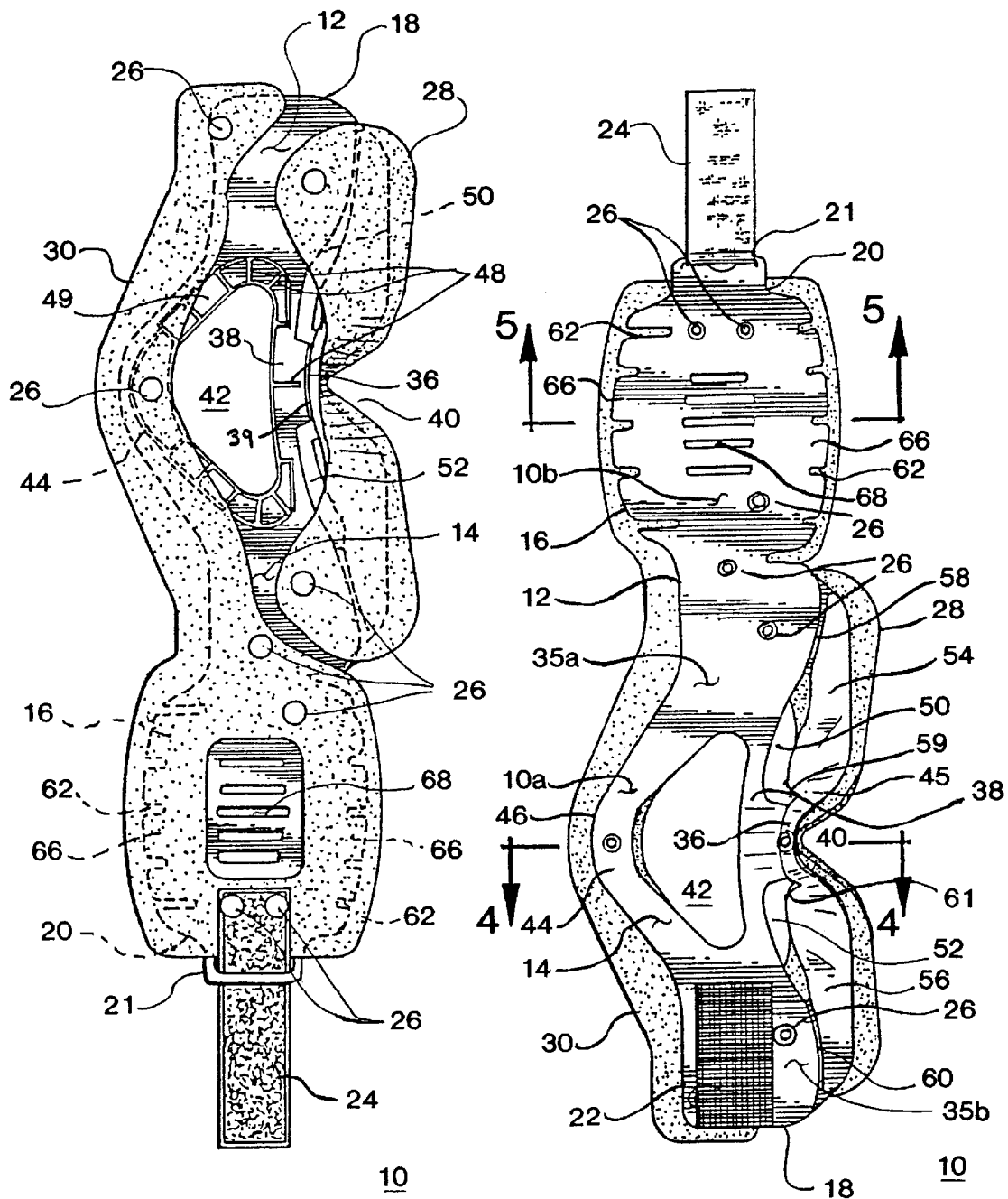
FIG. 1 is a top plan view of one side of a first embodiment of a cervical collar made in accordance with the present invention.
FIG. 2 is a bottom plan view of the opposite side of the collar of FIG. 1.

Referring now to the drawings, in which like reference numerals identify like elements throughout the several views, there is shown in FIG. 1 a one-piece cervical collar 10 of the present invention including a bendable front collar portion 10a, which defines a front side of the collar 10 in use, and a bendable back collar portion 10b, which extends unitarily from the front section 10a and defines a back collar portion 10b of the collar 10 when in use. The collar 10 preferably comprises a generally elongated bendable, unitary body 12 preferably fabricated by a molding process, and most preferably injection molded in one piece from a lightweight, flexibly resilient, substantially incompressible material, such as a suitable thermoplastic resin. Some suitable thermoplastic resins are high density polyethylene, polyurethane, polypropylene or the like. The molding process gives a three-dimensional, contoured shape to the elongated body 12, as described below. The body 12 includes a front body section 14 and a rear body section 16 which extends unitarily from one side of the front body section 14.

The collar 10 (and the unitary body 12) are of a length and flexibility sufficient to be wrapped into a tubular shape as shown in FIG. 6, with a free edge 18 of the front body section 14 at least adjoining a free edge 20 of the rear body section 16 so as to form unitary body 12 into a generally tubular shape. The unitary body 12 is preferably bendable, and even flexible, but sufficiently rigid to provide cervical support when wrapped into the tubular shape shown in FIG. 6. In accordance with one aspect of the present invention, the unitary body 12 is preferably molded in a substantially flat shape as shown in FIGS. 1 and 2. The flat shape of the unitary body 12 allows the collar 10 to be efficiently stacked atop similar collars 10.

The collar 10 includes a first fastener 22 attached to the front body section 14 proximal the free edge 12 and a second fastener 24 that cooperates with the first fastener 22, attached at the free edge 20 of the rear body section 16.

The first fastener 22 and the second fastener 24, are coupled with and preferably fixedly attached by suitable mechanical or chemical means, such as adhesives, rivets, stitching, welding, integral molding, etc., to the unitary body 12. The first fastener 22 is most preferably a Velcro® hook-type fabric fastening strip which is adhesively attached to the unitary body 12. The second fastener 24 is most preferably a Velcro® loop-type fastening strip which is attached to the unitary body by rivet fasteners 26. The second fastener 24 is preferably passed through a loop 21 unitarily molded into the extreme free edge 20 of the unitary body 12 and thus extends from the free edge 20 sufficiently to overlap and engage the first fastener (as shown in FIG. 6) when the elongated body 12 is wrapped into a tubular shape.

Figure 3:
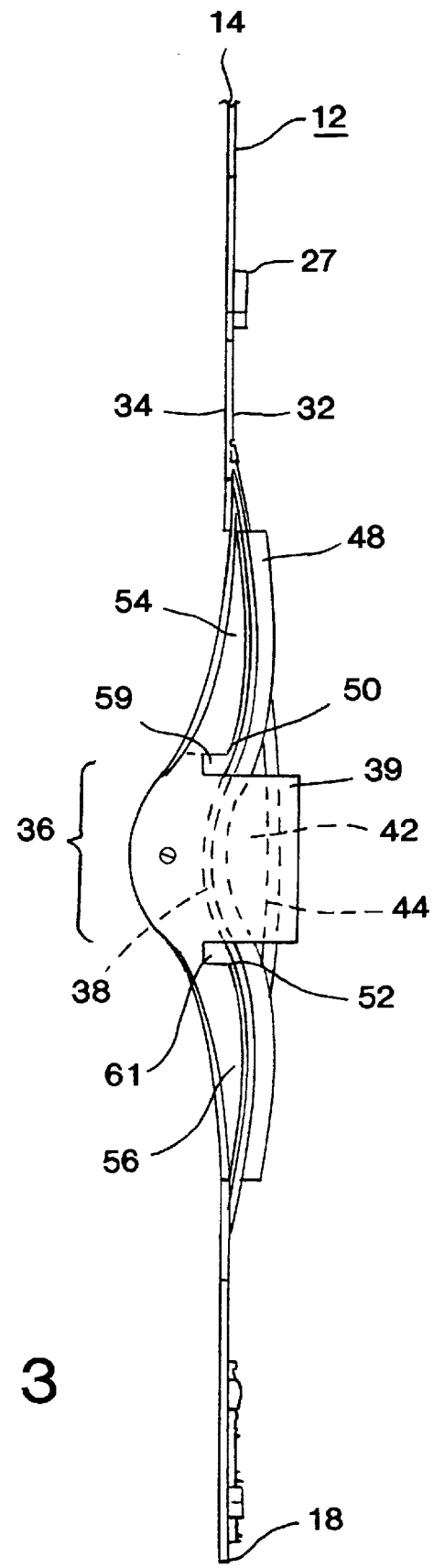
FIG. 3 is a side elevation view of the front body section of the collar of FIG. 1.

As seen in FIGS. 2 and 3, compressible flexible foam strips 28 and 30 are mounted on to a side 32 of the body 12 which forms an inner side of the collar 10 when wrapped into the tubular shape shown in FIG. 6. The foam strip 28 is preferably shaped to cover an upper portion of the front body section 14 and the foam strip 30 is preferably shaped to cover the lower portion of the front body section and the entire perimeter of the back body portion 16. The strips 28 and 30 are preferably permanently affixed to the side 32 of unitary body 12 by adhesives and/or mechanical fasteners, most preferably thermoplastic rivet fasteners 26, as shown.

As shown in FIG. 1, the front body section 14 includes a central portion molded to extend or project transversely outwardly between substantially flat side or "wing" portions 35a and 35b that form a substantially flat remainder of the front body section 14. The front body section 14 is preferably formed to be generally symmetric with respect to a centerline taken along section line 4—4. More preferably, an upper central portion 36 of the front body section 14 includes a transversely projecting support member 39, which is unitarily formed with an adjoining medial central portion 38, defining at least part of a transversely extending chin support 40 along the upper central portion 36 of the front body section 14.

An enlarged tracheal opening 42 is preferably medially located in the front body section 10a between the upper central portion 36 and a lowermost central portion 44 of the front body section 14. The front body section 14 includes an upper edge 45, and a lower edge 46 that conform to the sternum and clavicle area of a patient wearing the collar 10. Due to the central location and preferred enlarged size of the tracheal opening 42, it is desirable to reinforce the center of front body section 14 to prevent it from tending to collapse. Preferably, reinforcement is provided by means of a plurality of unitarily molded ribs 48, shown in FIG. 2, that extend unitarily and transversely from the main portion of the unitary body 12 proximal to, and preferably immediately adjoining, the tracheal opening 42. The plurality of ribs 48 preferably define closed-sided cells 49, extending along lateral sides of the tracheal opening 42. The ribs 48 tend to prevent collapse of the body 12 in a vertical direction (i.e., the axial direction when the collar 10 is formed into the tubular configuration of FIG. 6).

Referring again to FIG. 1, a pair of elongated openings 50 and 52 are preferably provided flanking either of two opposing sides of the transversely extending upper central portion 36. The openings 50 and 52 define a pair of corresponding laterally extending jaw support portions 54 and 56, respectively, of the front body section 14. Preferably, the jaw support portions 54 and 56 are each unitarily formed with the transversely extending upper central portion 36. Preferably, notches 59 and 61 are provided at the points of intersection between the jaw support portions 54 and 56 respectively, and the upper central portion 36. The notches 59 and 61 relieve the stress caused by the bending of the jaw support portions 54 and 56, as described below, and permit the collar 10 to form a shape that better fits the anatomy of each individual patient.

Each of the jaw support portions 54 and 56 extends from the upper central portion 36 toward the rear body section 16 and the free edge 18, respectively. The jaw support portion 54 connects to an upper distal end of side portion 35a and the jaw support portion 56 connects to an upper distal end of side portion 35b. Preferably, a separate unitary hinge is formed at the distal ends of the jaw support portion 54 and 56 to flexibly connect the jaw support portions 54 and to the upper distal ends of the side portions 35b and 35a, respectively. The hinges are preferably defined by grooves 58 and 60 which are preferably formed by a molding process that varies the thickness of the unitary body 12 in the vicinity of the grooves 58 and 60. The inclusion of grooves 58 and 60, allow the jaw supports 54 and 56 to twist from an initial orientation, at least partially co-planar with the adjoining side portions 35a and 35ba, to an orientation extending substantially transverse to the adjoining portion of the front body section 14, thereby conforming to each patient's unique jawline.

As explained above, both the rear collar portion 10b and rear body section 16 are preferably essentially flat. The rear body section 16 is preferably provided with a number of parallel slots 62, each of which extends transversely in the elongated body 12 inwardly from the "upper" and the "lower" edges of the rear body section 16. The slots 62 may have uniform length, or a varying length, as depicted in FIG. 1. Whether of uniform length or of varying length, the slots 62 define a plurality of fingers 66. The fingers 66 having the longest length are most easily bent and contribute to the overall flexibility of the rear body section 16 around the wearer's neck permitting the lower edge of the rear body section 16 to more readily conform to the back and shoulder area of the wearer. A plurality of centrally located openings 68 may also be provided to permit air circulation through the rear body portion 16 while the collar 10 is being worn. The openings 68 also enhance the flexibility of the rear body section 16.

Fabricating the unitary body 12 by a molding process enables certain selected portions of the body 12 to have a three-dimensional shape or configuration and to also have a varying thickness. Preferably, the three-dimensionally contoured parts of the elongated body 12 are: (1) the upper central portion 36, (2) the adjoining lateral jaw support portions 54 and 56 (to the extent needed to extend those portions from central portion 36 to their opposing distal ends where the jaw support portions 54 and 56 are essentially co-planar with the side portions 35a and 35b, (3) the plurality of molded ribs 48 reinforcing the body around the tracheal opening 42, and (4) a plurality of rivet bosses 27, that are preferably provided, as seen in FIG. 4, to reinforce the openings through which the stem of each rivet fastener 26 passes. The remaining portions of the elongated body 12 are preferably substantially flat before being wrapped into a tubular shape and, therefore, preferably have a uniform thickness. Also, as seen in FIG. 4, each of the reinforcement ribs 48 preferably has a substantially equal thickness and depth.

Referring now to FIGS. 1–4, the medial central portion 38 of the body 12 in the region above the tracheal opening 42 and below the upper support member 39 is preferably molded in an outwardly curved configuration. Preferably, the medial central portion 38 forms an arc that extends transversely outwardly beyond the outward extent of the lowermost central portion 44 and the remaining side portions 35a and 35b (seen in FIGS. 1–2). As such, the upper support member 39 and the medial central portion 38 are pre-configured into substantially the same shape both when the body 12 is wrapped into a tubular shape (FIG. 6) and also when body 12 is applied about the neck of a patient. In other words, the medial central portion 38 is preferably pre-molded into its final shape and, because it does not have to flex into a final shape, can be made thicker than the remainder of the body 12.

The increased thickness of the medial central portion 38 enhances the rigidity of the collar 10, and the support provided by the upper central portion 36, and further reduces the tendency of the tracheal opening 42 of collapsing.

The medial central portion 38 of conventional "flat" collars, which must be bent into a final shape, must necessarily have a thickness that is less than the "pre-molded" medial central area 38 of the present invention. As such, the chin support of conventional flat collars is less stable.

It is contemplated that the medially central portion 38 preferably will remain in substantially the same arc independent of the degree that the body 12 is bent when the collar 10 is applied about the neck of a patient Also, the degree of chin support provided by the prior art "bendable" lower central areas depends on the degree of bend of the collar body, because the degree of bend of the medial central portion affects the angle of the chin support.

As is further seen in FIGS. 3–4 and the fragmentary cross-section of FIG. 7, the upper support member 39 preferably includes an outer chin support member portion 39a and an inner chin support member portion 39b which are unitary. Outer chin support member portion 39a extends beyond the outer extent of medial central portion. 38 and inner chin support member portion 39b projects within the outward extent of medial central portion 38.

As is best seen in cross-section in FIG. 4, a generally T-shaped joint is formed between the transversely extending chin support member 39 and the underlying medial portion 38 of the body 12. Also, outer chin support portion 39a extends slightly upwardly as it projects transversely outwardly from the outer side 34 of the elongated body 12 while inner chin support portion 39b extends slightly downwardly as it projects from the inner side 32 of the elongated body 12..

The jaw support portions 54 and 56 extend laterally from the outer chin support portion 39a forward of the adjoining medial portion 38 and the remainder of the elongated body 12. Together, as shown in FIG. 6, upper central portion 36 and the lateral upper edge portions 54 and 56 define a partially upwardly concave mandible support 70.

The upper central portion 36 defines a chin support 40 that substantially prevents a forward or downward movement of the wearer's chin, while the jaw support portions 54 and 56 define the remainder of the mandible support 70 and simultaneously (but independently) prevent lateral mandible movement.

As best seen in FIGS. 4 and 7, which are cross-sectional views of the upper central portion 36 before and after wrapping, respectively, the partial concavity of the chin support 40 is increased as the collar 10 is flexed from its initial substantially flat configuration shown in FIGS. 1–5 to the tubular configuration shown in FIGS. 6–7. The chin support members 39a and 39b pitch more steeply when the front body section 14 is flexed, and the unitary hinges formed by grooves 58 and 60 further permit the jaw support portions 54 and 56 to deflect outwardly by a degree sufficient to accommodate the unique jaw line of a wearer. Preferably, the outermost portions of the front section 14 along the upper edge 45 are scalloped upwardly so as to cover the temporamandible joint area of the wearer and to assist in immobilizing the jaw as well as the cervical region.

The present invention also discloses fabricating a flat collar by molding, preferably by injection molding, to permit the formation of a very strong, relatively rigid, three-dimensional thermoplastic chin support and also permit a very strong, yet flexible mandible support capable of contouring to the unique jaw line of a wearer. Molding the front body portion 14 permits the outer chin support portion 39a to project outwardly and the inner chin support portion 39b to project inwardly from medial central portion 38. This configuration provides a stiffer, more stable, and more comfortable chin and mandible support and restraint than that is provided by the more flexible structure of the prior art cervical collars described above.

An additional advantage of the collar 10 of the present invention is that it takes up considerably less storage space than conventional collars. Without packaging or with proper packaging, a plurality of collars 10 may be nested so that each projecting upper central portion 36 and each transverse projections 39a and 39b nest, thereby presenting a minimum of storage difficulties.

The ability to transversely extend the upper central portion 36 from the remainder of body 12 greatly improves the ability to control the immobilization of the wearer's head. Preferably, the front projecting portion 39a of the upper central portion 36 is pivoted at an angle A, seen in FIG. 4, preferably about 110°, with respect to the adjoining medial portion 38 and the remainder of the unitary body 12. The greater transverse extent of the central portion 36, together with the upward pitch of member 39, provides a better fit to and substantial support for the front of a wearer's chin.

The body 12 is, therefore, preferably injected molded from a bendable, substantially incompressible (i.e. non-foamed) thermoplastic resin such as high density polyethylene. In contrast, the flexible foam strips 28 and 30 are preferably composed of a hydrophobic foam, such as polypropylene or polyurethane, which prevents the absorption of bodily fluids and allows the collar to be more readily disinfected and reused. Alternatively, hydrophilic foam plastic materials, such as polyesters, may be used which absorb bodily fluids from the wearer and improve comfort. The use of either type of foam plastic strips lessens the transmittal of pressure from the elongated body 12 to the wearer's face.

The foam strips 28 and 30 may be cut from a flat plastic sheet material. Preferably, the upper and lower edge margins of the foam strips 28 and 30 are formed to extend beyond the upper and lower edge margins of the unitary body 12 presenting a foam material edge against the wearer's body improving comfort. Two foam strips are preferred to one continuous strip since two strips provide the best possible fit on the body 12. In particular, the upper strip 28, which defines the lining of the mandible support 70, better conforms to the curved surface of the mandible support 70 when it is formed separately from the lower strap 30. Also, the medial upper central portion 36 is preferably pierced to receive a flat-headed rivet which secures the upper foam strip 28 to the upper central portion 36.

Figure 10:
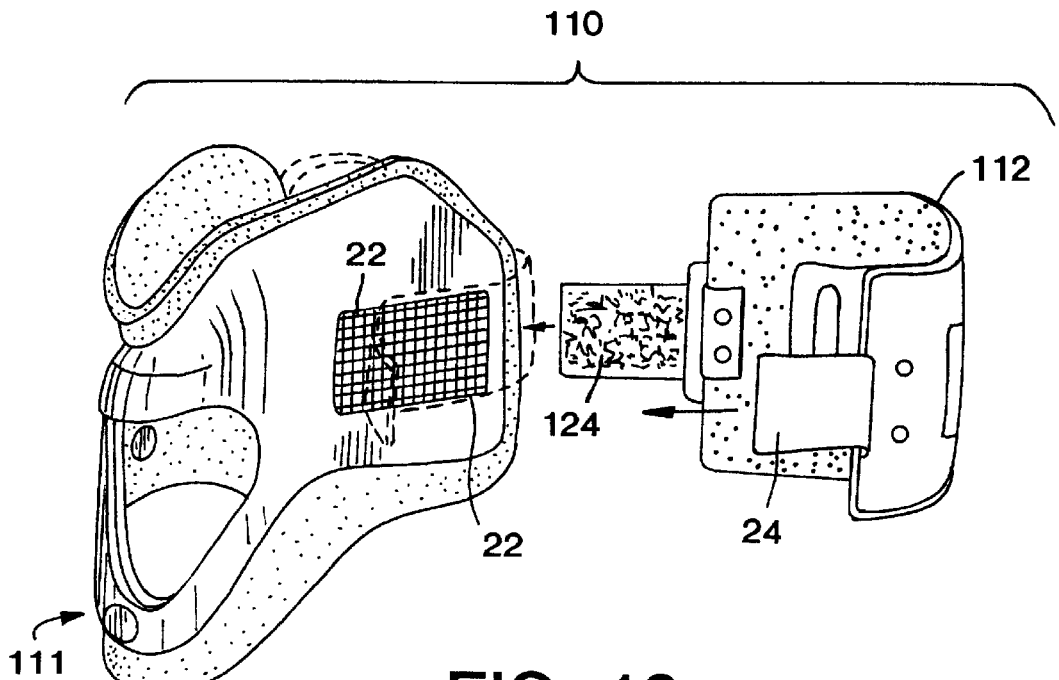
FIG. 10 is a perspective view of the collar of FIGS. 8–9.
Figure 11:
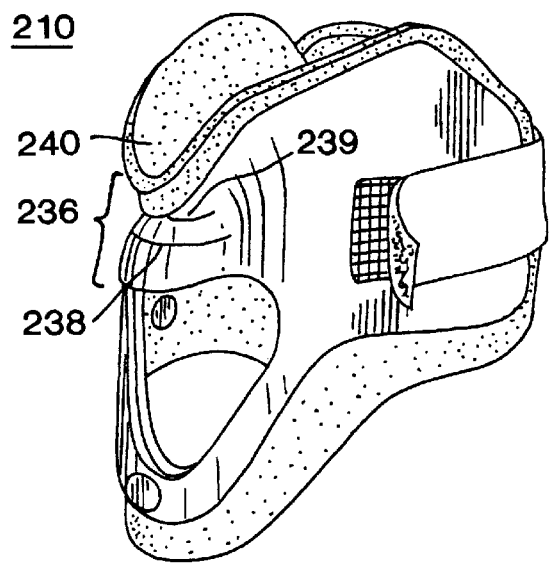
FIG. 11 is a perspective view of the collar of FIGS. 8–9 wrapped into a tubular shape as it would be when worn.

Although not shown, a breathable natural fabric cover or liner can be provided on the inner side of the collar 10 by permanently affixing the liner over the foam strips 28 and 30 to the body 12 or removably mounting the liner on the collar 10. FIGS. 8–10 illustrate a second embodiment of a cervical collar 110 that is also constructed in accordance with the present invention, and classified as a "hybrid two-piece" collar. As seen in FIGS. 8B and 9A, the collar 110 is formed by an substantially flat front collar half 110a and a substantially flat rear collar half 110b, shown in FIGS. 8A and 9B. Front collar half 110a includes a front body section 114, preferably molded from an essentially incompressible thermoplastic material. Rear collar half 110b includes a rear body section 116 formed separately from the front body section 114 and preferably similarly molded from the same or a similar material.

The two halves 110a and 110b form the front and rear sides, respectively, of the collar 110 when the collar 110 is wrapped around a wearer's neck. When wrapped, a first free edge 18 of the front body section 114 adjoins a first free edge 20 of the rear body section 116, while a second free edge 118 of the front body section 114 adjoins a second free edge 120 of the rear body section 116 so as to form the substantially tubular shape of the collar 110, seen in FIG. 10.

The collar 110 also includes a first fastener 22 and a second fastener 122, both preferably Velcro® hook-type fastening members, mounted to and preferably fixedly attached by suitable mechanical or adhesive means, proximal to the free edge 18 and the free edge 118, respectively, of the front body section 114. A third fastener 24 and a fourth fastener 124, preferably Velcro® loop-type fastening members, are mounted to and preferably fixedly attached by suitable mechanical or adhesive means, proximal of the free edges 20 and 120, respectively, of the rear body section 116 and matingly engage with the hook-type fasteners preferably used in the first and second fabric fastener strips 22 and 122.

Third fastener 24 and fourth fastener 124 pass through loops 21 and 121, respectively, which are preferably unitarily molded at the extreme free edges 20 and 120, respectively, of the rear body portion 116. Third fastener 24 and fourth fastener 124 extend from the free edges 20 and 120, respectively, by an amount sufficient to overlap the first fastener 22 and second fastener 122, respectively, when the collar 110 is wrapped into the tubular shape.

Apart from the provision of the additional releasable fasteners 122 and 124, loop 121, and the separate front and rear body portions 114 and 116, collar 110 is otherwise substantially identical to collar 10.

FIGS. 12–13 illustrate a third embodiment of a one-piece, flat cervical collar 210 constructed in accordance with the present invention. The cervical collar 210 is substantially similar to the collar 10 described above, with like numerals identifying similar elements. However, unlike collar 10, collar 210 is not provided with the elongated openings 50 and 52, the grooves 58 and 60, and the notches 59 and 61 present in collar 10. As a result, jaw supports 254 and 256 are unitarily molded with the remainder of an elongated body 212, providing increased lateral support for the mandible when the collar 210 is wrapped around a wearer's neck, as shown in FIG. 1. As seen in FIGS. 12–13 the chin support 240 and the overall mandible support 270 formed along the upper side of the front collar portion 210a are also mated with the protruding upper central portion 236. It should also be understood, however, that collar 210 may be fabricated as a hybrid two-piece collar similar to collar 110.

FIGS. 14–21 illustrate additional embodiments of cervical collars constructed in accordance with the present invention. Among other things, these embodiments illustrate various ways in which the present invention can be incorporated or retrofitted into existing cervical collars. FIGS. 14–16, for example, depict flat, one-piece cervical collars 310, 410, and 510, respectively, in which progressively smaller unitary molded bodies 314, 414, and 515, respectively are provided. In the collar 310, the front collar section 310a includes a front body portion 314, substantially identical to the front body portion 114 of the collar 110 except for the deletion of the fastener strip 122. A second fastener strip 24 is attached, instead, directly to a compressible, flexible foam strip 330 forming the entirety of the rear collar portion 310b and extending unitarily on to the inner side of front body portion 114 and attached by suitable means, such as the rivet fasteners 26 described above. A pair of identical looped members 321 are preferably applied to either side of the foam strip 330 to spread the attachment loads over a broader area. Air holes 368 substitute for the slots 68 of collar 10 to maintain ventilation in the rear collar half 310b.

FIG. 15, illustrates an embodiment of a cervical collar 410 that includes a substantially one-piece compressible, flexible foam body 430 defining a front collar portion 410a and a unitary rear collar portion 410b. Preferably, a shortened support body 414 fabricated from a plastic resin, is mounted and secured to an upper portion of the front collar portion 410a by suitable means, such as rivet fastener 26. The body 414 defines a mandible support 470, and includes an upper central portion 436 protruding outwardly from the remainder of the collar 410 and including along its central upper edge, a protruding medial central portion supporting a transversely extending member 439 defining at least part of a chin support 440. Elongated openings 50 and 52 define, in part, jaw support portions 54 and 56, respectively, flexibly connected at their distal ends by living hinges, defined by grooves 58 and 60 as described above in connection with collar 10. Due to the decreased vertical support resulting from the limited extent of the mandible support 470, a tracheal opening 442 is provided which is smaller than the opening 42 of collar 10. Also, fastener strip 22 is again secured directly to foam strip 430, preferably by rivet fasteners 26 as described in connection with collar 310.

FIG. 16 depicts a one-piece, flat collar 510 which comprises a unitary, flexible, compressible foam body 530 which is minimally reinforced by a front body portion 536 located in an upper central area of the front half 510a of the collar 510. The front body portion 536 includes a transversely extending upper support member 539 supported by a generally partial concave medial central portion 538, which is itself mounted by suitable means such as a rivet fastener 526 to the foam body 530 thereby defining a chin support 540. Mandible support is provided by upper edge portions 554 and 556 of the foam body 530. Otherwise, the indicated changes are similar to those incorporated into the embodiments of FIGS. 14–15.

Another cervical collar 610 is illustrated in FIG. 17, and differs from the prior embodiments of FIGS. 1–16 in that a separate mandible support member 670 is attached to a separate molded unitary body 612 by suitable means, such as rivet fasteners 626. The unitary body 612 is again, however, substantially flat. An upper, centrally located portion 638 of a front body section 614 of the substantially flat unitary body 612 is coupled with, and preferably fixedly attached to, a chin support portion 639 of the mandible support 670 through a laterally curved base 639c. The base or base portion 639c is preferably molded unitarily with and supports both the outwardly and the inwardly transversely extending chin support projections 639a and 639b. Also, lateral jaw supports 654 and 656 are unitarily formed with and extend away from the projecting chin support projections 639a and 639b and foam strip 628 and define the remainder of the flexible mandible support 670.

Figure 18:
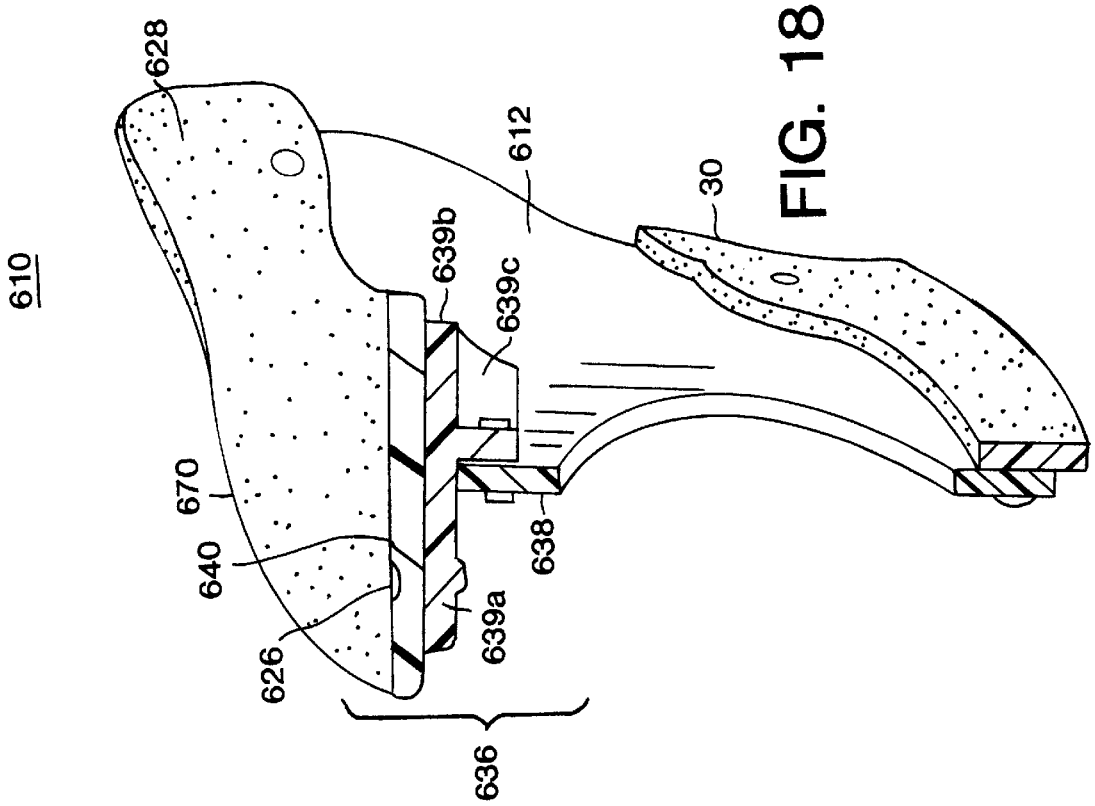
FIG. 18 is a fragmentary, cross-sectional view of the cervical collar of the present invention, taken along the lines 18—18 of FIG. 17, illustrating the addition of a transverse chin support member.

FIG. 18 depicts the manner in which the transversely extending projections 639a and 639b are preferably secured to the upper centrally located portion 638 of the unitary body 612. As shown, the projections 639a and 639b define (along with compressible foam strip 628), a chin rest portion 640 of an overall mandible support 670.

Figure 19:
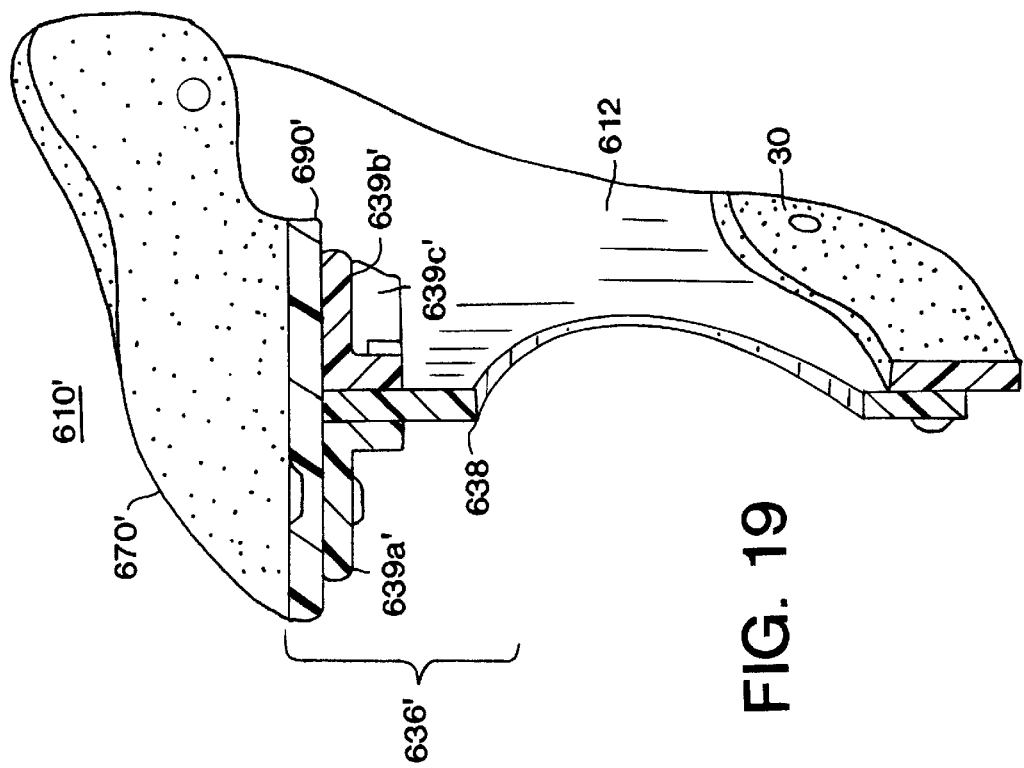
FIG. 19 is a fragmentary, cross-sectional view of the flat cervical collar of the present invention, similar to FIG. 18, illustrating an alternate embodiment transverse chin support member.

FIG. 19 shows an alternative embodiment of the cervical collar 610 shown in FIGS. 17–18. Collar 610' includes a molded mandible support member 670' having only a forwardly extending and centrally located transverse projection 639a'. Projection 639a' is attached to an outer side of an upper central member 638, while a separate, inwardly extending transverse chin support projection 639b' is attached to the opposing, inner side of the upper central portion 638 of the unitary body 612. The downwardly extending bases or legs of the transverse projections 639a and 639b are preferably outwardly curved.

Figure 20:
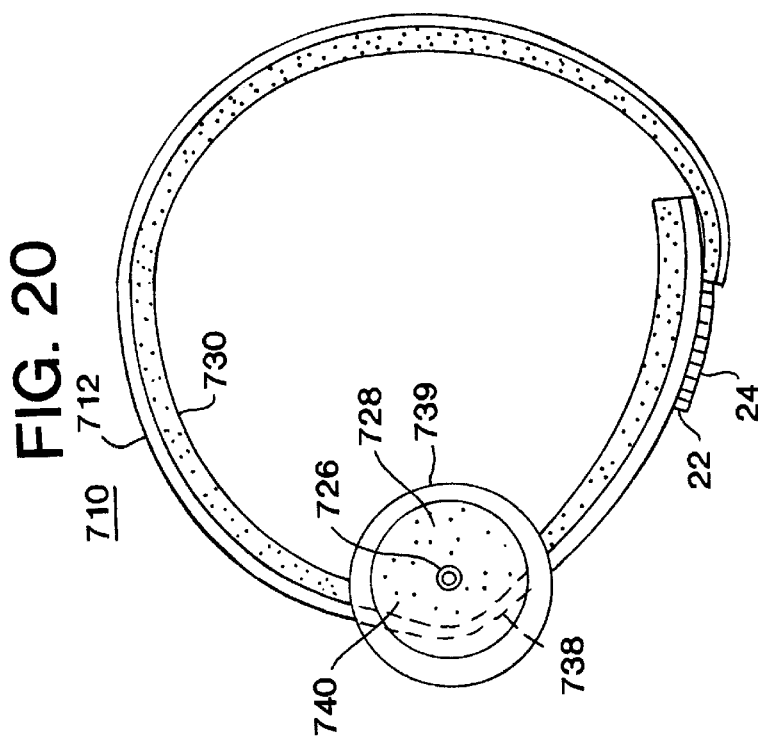
FIG. 20 is a plan view of the collar of FIG. 17 after being wrapped into a tubular form.

In addition to providing full mandible support, it will be appreciated that a simple transverse chin support member 740 similar to portions 639a–639c or portions 639a' and 639b' can be mounted to the upper central portion 738 of the front portion 714 of an otherwise conventional cervical collar 710 lacking the lateral portions which form a transversely extending chin support 740, as seen in FIG. 20. In this embodiment, an otherwise flat cervical collar 710, which includes a molded unitary body 712 mounted to a compressible foam strip 730 on its inner side, includes a chin support 740 that preferably extends both forwardly and rearwardly from the underlying supporting portion 736.

Figure 21:
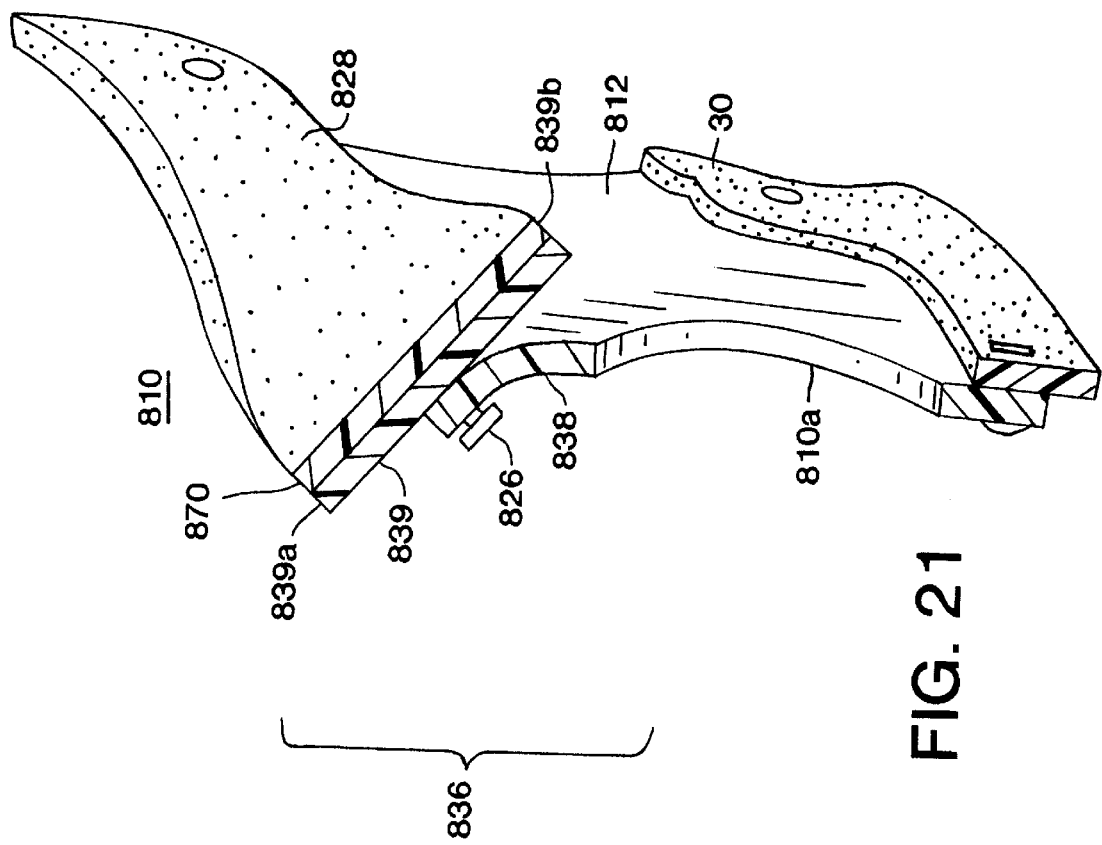
FIG. 21 is a broken away, localized cross-sectional view of a cervical collar illustrating another alternate embodiment of a transversely extending chin support member.

FIG. 21 depicts yet another embodiment of cervical collar 810 showing an alternate method of mounting a mandible support member 870. The mandible support 870 has a central, curved, and transversely extending chin support portion 839 defining transversely extending chin support projections 839a and 839b, similar to the mandible support. The mandible support 870 is affixed using a rivet 826, or any other suitable attachment, to connect the chin support 839 to a flexible upper central portion 838 of a molded unitary body 812, as might be provided in a conventional flat one-piece or hybrid two-piece collar. The resulting structure defines a projecting upper central portion 836 on the front collar portion 810a. Since conventional flat one-piece and hybrid two-piece collars generally provide inadequate chin support due to their inherent design limitations as described in detail above, the addition of a premolded, curved, transverse chin support portion 839, including inner chin support projection 839b, would provide additionally needed stiffness and support under the chin of a wearer.

Figure 22:
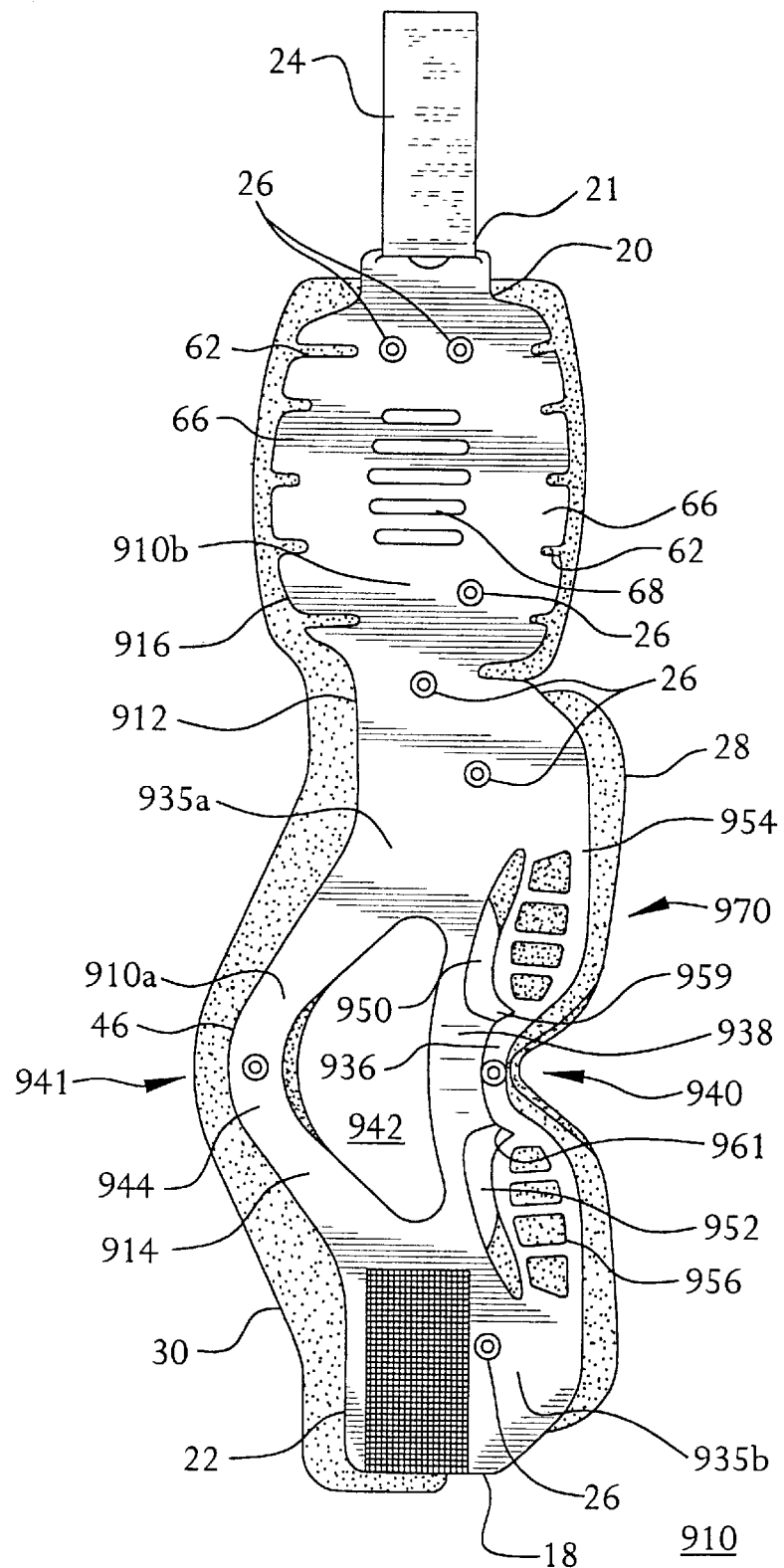
FIG. 22 is a top plan view of a seventh embodiment of a cervical collar of the present invention.
Figure 23:
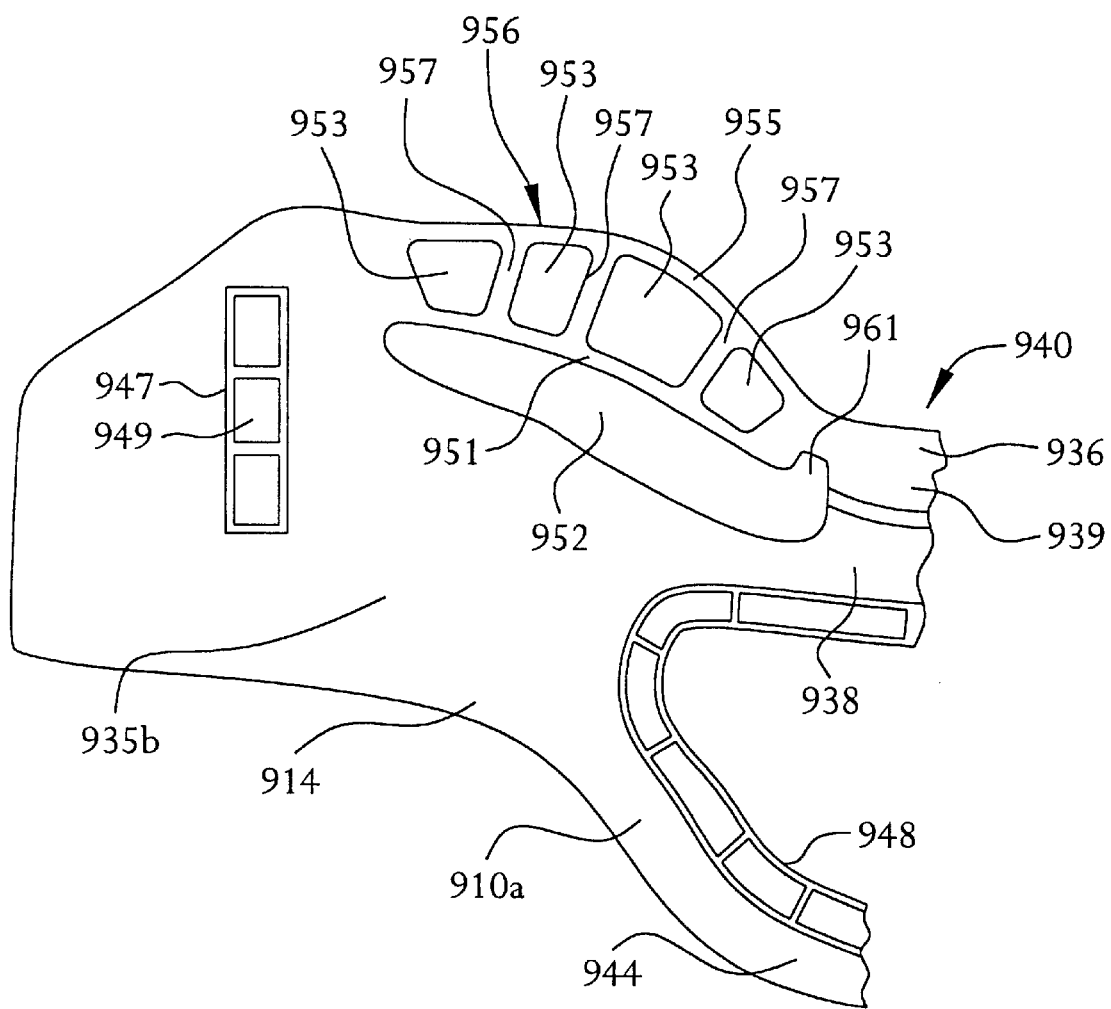
FIG. 23 is a fragmentary bottom plan view of the collar of FIG. 22.

In FIGS. 22 and 23, another cervical collar embodiment 910 is shown. The cervical collar 910 includes a substantially flat bendable front collar portion 910a and a bendable back collar portion 910b that preferably extends unitarily from the front collar portion 910a. The collar 910 comprises an elongated bendable unitary body 912 preferably fabricated by a molding process. The molding process is most preferably an injection molding process that allows the body 912 to be molded in one piece from a lightweight, flexible resilient, substantially incompressible material, such as a suitable thermoplastic resin like high density polyethylene or polyurethane. The body 912 comprises a front body section 914 and a rear body section 916.

The front body section 914 includes a central portion 941 that is molded to extend or project transversely outwardly from between an essentially flat side or "wing" portion 935a and an essentially flat side or "wing" portion 935b. The side portions 935a and 935b form an essentially flat remainder of the front body section 914.

The central portion 941 includes an upper central portion 936, an adjoining medial central portion 938, a lower central portion 944, and an enlarged tracheal opening 942. The upper central portion 936 includes a transversely extending chin support 940, which comprises a transversely extending support member 939 (FIG. 23). The support member is preferably unitarily formed with the adjoining medial central portion 938. Chin support 940 is substantially similar to the chin support 40 as described above in connection with FIG. 1.

An elongated opening 950 and an elongated opening 952 are preferably provided flanking either side of the upper central portion 936 and the medial central portion 938. A jaw support member 954 extends laterally between the upper central portion 936 and an upper distal end of the side portion 935a. Similarly, a jaw support member 956 extends laterally between the upper central portion 936 and an upper distal end of side portion 935b.

The jaw support members 954 and 956 are preferably unitarily formed with the elongated body 912. Preferably, stress relieving notches 959 and 961 are provided at the points of intersection between the jaw support members 954 and 956, respectively, and the upper central portion 936. The jaw support members 954 and 956 along with the chin support 940 together form a mandible support 970.

As best seen in FIG. 23, a plurality of openings 953 are formed in the jaw support member 956 to facilitate the bending of the jaw support member 956 to conform to each wearer's unique jaw line. The openings 953 preferably have a polygonal shape with filleted corners for relieving stress but it is understood that they may be of any shape that allows the jaw support member 956 to remain flexible yet provide sufficient jaw support. The openings 953 are positioned in the jaw support member 956 to form a lower lateral rail 951, an upper lateral rail 955, and a plurality of transverse rails 957. The lower lateral rail 951, the upper lateral rail 955 and the plurality of transverse rails 957 form a frame that allows the jaw support member 954 to bend and conform to the wearer's jaw line yet provide sufficient support to immobilize the wearer's head against excessive lateral movement. Preferably, the rails 951, 955, and 957 have a width of at least 3/16 inch. Similarly, as seen in FIG. 22, a plurality of openings 953 forming rails 951, 955, and 957 are also formed in the jaw support member 954 to facilitate the bending of the jaw support member 954.

The inclusion of openings 953 impart sufficient flexibility to the jaw support members 954 and 956 such that there is no need to provide grooves at the distal end of the wing portions 935a and 935b, such as the grooves 58 and 60 provided in the collar 10 (FIG. 1).

It has been found that a collar bodies 912 provided with openings 953 in the jaw support members 954 and 956 can better withstand any stress concentrations caused by the bending of the collar body 912. It appears that the openings 953 allow the thermoplastic resin to flow through the flow more evenly through the collar body 912 during the injection molding process since there are no reduced thickness portions, such as grooves 58 and 60 that could, under certain conditions, restrict the flow of molten thermoplastic. As a result, the thermoplastic material of the cervical collar body 912 "knits" together better during the molding process resulting in collar body which is more resistant to tearing and stress failure.

In all other aspects, the cervical collar 910 is identical to the collar 10 described in connection with FIG. 1. The collar 910 is also applied to a patient in a manner similar to the collar 10.

Also, as seen in FIG. 23, ribs 947 can be optionally provided near the distal ends of side portion 935a (not shown) and side portion 935b. Preferably, the plurality of ribs 947 define closed-sided cells 949 similar to the cells of ribs 48 and 948 and are unitarily molded with body section 914. This arrangement tends to prevent the collapse of the body 912 in a vertical direction (i.e., the axial direction when the body 912 is in a tubular configuration). This arrangement also allows the body 912 to be made thinner, reducing the amount of thermoplastic resin needed.

Finally, it should also be understood that any of the previously described one-piece collars may be fabricated as a "hybrid two-piece" collar as explained above with reference to FIGS. 12–13.

While certain preferred embodiments and various modifications thereto have been described or suggested, other changes in these preferred embodiments will occur to those of ordinary skill in the art which do not depart from the broad inventive concepts of the present invention. Accordingly, reference should be made to the appended claims rather than the specific embodiment of the foregoing specification to ascertain the full scope of the present invention.

What is claimed is:

1. A cervical collar comprising:
   a collar body having a front body portion and a rear body portion;
   a separate chin support coupled to the collar body for supporting the chin of a patient, the collar body and the chin support being fabricated from a substantially incompressible plastic material, the cervical collar having a substantially flat shape and being bendable into a substantially tubular shape;
   a fastener connected to the collar body for attaching an end of the rear body portion to an end of the front body portion to hold the collar body in the substantially tubular shape;
   the chin support comprising a central transverse portion which extends laterally from the front body, a first side portion and a second side portion which extend laterally from either side of the central transverse portion, and a base portion which extends downwardly and transversely from the central transverse portion, the base portion extending laterally across the front portion of the collar body and being coupled thereto, the base portion being unitary with the central transverse portion; and
   a tracheal opening formed in the front body portion of the collar body.

2. The cervical collar according to claim 1, wherein the base portion is fixedly attached to the collar body by at least one fastener.

3. The cervical collar according to claim 1 further comprising a foam strip attached to an inner side of the chin support.

4. The cervical collar according to claim 1 further comprising a second foam strip attached to the collar body.

5. The cervical collar according to claim 1, wherein each end of the laterally extending base portion is attached to the collar body by at least one fastener; each end of the laterally extending base portion forming a part of one of the side portions.

6. The cervical collar according to claim 1, wherein the transverse portion comprises an outer chin support projection and an inner chin support projection, the outer chin support projection extending transversely beyond an outward extent of the base portion and the inner chin support extending transversely within the outward extent of the base portion.

7. A cervical collar comprising:
   a collar body having a front body portion and a rear body portion, the collar body having a substantially flat shape and being bendable into a substantially tubular shape, the collar body being fabricated from a substantially incompressible plastic material;
   a fastener connected to the collar body for attaching an end of the rear body portion to an end of the front body portion to hold the collar body in the substantially tubular shape;
   a separate chin support coupled to the collar body for supporting the chin of a wearer, the chin support being fabricated from a substantially incompressible plastic material, the chin support comprises a central transverse portion which forms a chin cup, side portions which extend laterally from either side of the central transverse portion, and a base portion which extends downwardly and laterally from the central transverse portion, the base portion being unitary with the central transverse portion, the base portion extending laterally across the front body portion, each laterally extending end of the base portion forming a lower portion of one of the side portions, the lower portions being coupled to the front body portion; and
   a tracheal opening located in the center of the front of the cervical collar.

8. The cervical collar according to claim 7, wherein the base portion is fixedly attached to the collar body by at least one fastener and prevents relative movement therebetween.

9. The cervical collar according to claim 7, further comprising a foam strip attached to an inner side of the chin support.

10. The cervical collar according to claim 7, further comprising a second foam strip attached to the collar body.

11. The cervical collar according to claim 1, wherein the transverse portion comprises an outer chin support projection and an inner chin support projection, the outer chin support projection extending transversely beyond an outward extent of the base portion and the inner chin support extending transversely within the outward extent of the base portion.

* * * * *